United States Patent [19]
Gåserød et al.

[11] Patent Number: 6,165,503
[45] Date of Patent: Dec. 26, 2000

[54] HIGH STRENGTH CAPSULES, PROCESS OF PREPARING AND USING THE SAME

[75] Inventors: Olav Gåserød, Trondheim; Øivind Skaugrud, Mjøndalen, both of Norway; Peter Dettmar, East Yorkshire, United Kingdom; Gudmund Sjåk-Braek, Trondheim, Norway; Ian Jolliffe, East Yorkshire, United Kingdom

[73] Assignee: FMC Biopolymer A.S., Drammen, Norway

[21] Appl. No.: 09/108,809

[22] Filed: Jul. 1, 1998

[30] Foreign Application Priority Data

Jul. 7, 1997 [GB] United Kingdom .................... 9714293

[51] Int. Cl.⁷ .............................. A61K 9/48; A61K 9/66; A61K 9/52

[52] U.S. Cl. .......................... 424/463; 424/451; 424/452; 424/455; 424/457; 514/962; 514/964

[58] Field of Search .................... 424/451, 457, 424/463, 452, 455; 514/962, 964

[56] References Cited

U.S. PATENT DOCUMENTS

| | | |
|---|---|---|
| 4,352,883 | 10/1982 | Lim .......................................... 435/178 |
| 4,409,331 | 10/1983 | Lim .......................................... 435/178 |
| 4,663,286 | 5/1987 | Tsang et al. ............................. 435/178 |
| 4,690,682 | 9/1987 | Lim .......................................... 604/891 |
| 4,749,620 | 6/1988 | Rha et al. . |
| 4,808,707 | 2/1989 | Daly et al. . |
| 4,950,600 | 8/1990 | Tanaka et al. . |
| 5,116,747 | 5/1992 | Moo-Young et al. . |

FOREIGN PATENT DOCUMENTS

| | | |
|---|---|---|
| 0 152 898 | 8/1985 | European Pat. Off. . |
| 0 173 751 | 3/1986 | European Pat. Off. . |
| 2 046 209 | 11/1980 | United Kingdom . |
| 91/09119 | 6/1991 | WIPO . |

OTHER PUBLICATIONS

O. Smidsrød et al., "Alginate as Immobilization Matrix for Cells", TIBTECH, vol. 8, No. 3, pp. 71–78 Mar. 1990.

*Primary Examiner*—Gollamudi S. Kishore
*Assistant Examiner*—Brian K. Seidleck
*Attorney, Agent, or Firm*—Patrick C. Baker; Wenderoth, Lind & Ponack, L.L.P.

[57] ABSTRACT

In the formation of capsules having a polyanionic polysaccharide core and a polycationic polysaccharide membrane layer, improved binding of the polycationic polysaccharide is achieved by including polyvalent ions, especially calcium ions, at the membrane forming step.

45 Claims, 16 Drawing Sheets

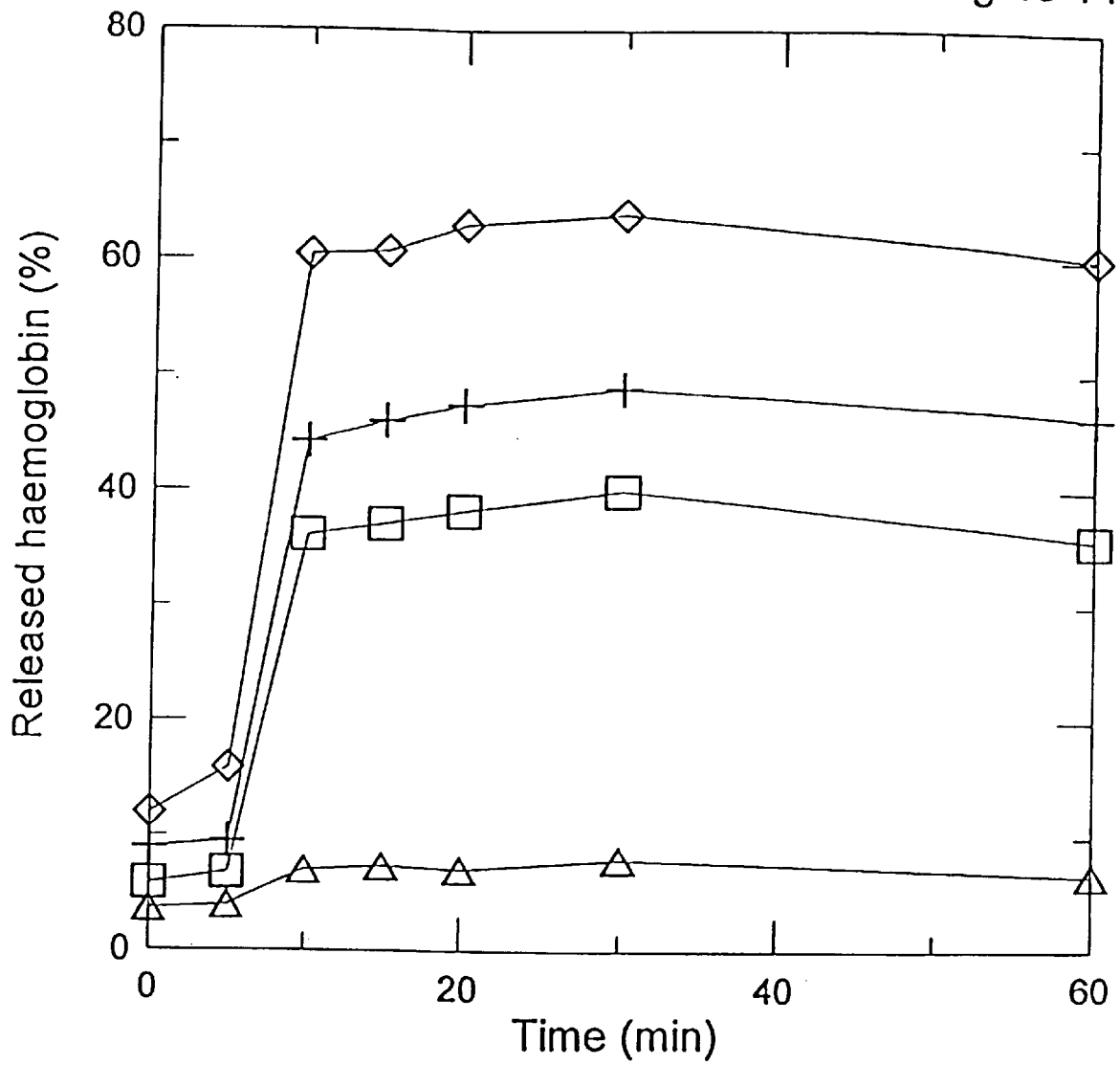
Figure 14
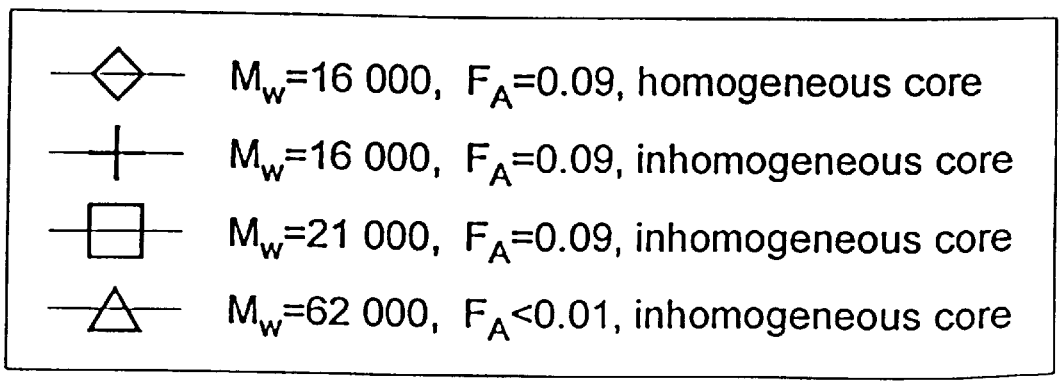

HIGH STRENGTH CAPSULES, PROCESS OF PREPARING AND USING THE SAME

BACKGROUND OF THE INVENTION

1. Field of the Invention

The present invention-relates to capsules, in particular microcapsules, comprising a polyanionic bead core and a polycationic membrane, and to a process for their production. More especially, the invention relates to such capsules having a higher strength and to a process for their formation.

2. Description of Related Art

Capsules consisting of a gelled polyanionic core and a polycationic membrane are known in the art and examples have comprised a core of an alginate and a membrane layer of poly-L-lysine. Capsules having a membrane layer comprising chitosan are also known. Such capsules have found various uses, such as the encapsulation of cells or other biological matter, (as described in "Alginate as immobilisation matrix for cells", Olav Smidsrød, Gudmund Skjak-Braek, TIBTECH, March (1990), Vol. 8, No. 3[74]), in drug delivery, especially sustained release drug delivery, and also have other agricultural and industrial uses.

Alginates are salts of alginic acids which are linear polysaccharides consisting of (1–4) bound residues of β-D-mannuronic acid ("M units") and α-L-guluronic acid ("G units"). Alginate polymers may consist of homopolymeric sequences of mannuronic acid residues ("M blocks"), homopolymeric sequences of guluronic acid residues ("G blocks") and sequences including both mannuronic and guluronic acid residues ("MG" blocks). Alginates will usually contain all three types of block each comprising from about three to about twenty monomer units. The distribution and relative quantities of the M and G units influences the properties of the alginate, and depends on the source of the alginate. Alginates are most commonly extracted from various types of algae.

Alginate gels can be formed by cross-linking the alginate polymer units and suitable cross-linking agents are polyvalent or divalent (hereinafter polyvalent) cations, in particular $Ca^{2+}$ and $Al^{3+}$.

A particular advantage, especially in relation to biological matter, of capsules prepared from polysaccharides, such as alginates, is that the encapsulation can be performed under mild conditions. Thus, gelling of alginate can take place at room temperature and in aqueous conditions. The procedure is rapid and does not require organic cross-linking agents or solvents. Alginates also have the particular advantage of being non-toxic and suitable for use in food and as pharmaceutical adjuvants or excipients.

Although alginate beads per se have been considered for uses such as sustained drug delivery, alginates have significant disadvantages in terms of stability and porosity. Alginates are biodegradable and alginate gels are reversible ionic networks which can be destabilised by calcium sequestering agents, such as citrates and phosphates, and also by non-gelling ions, such as $Na^+$ and $Mg^{2+}$. Also, the pore structure of the alginate gel is unsuitable for sustained drug delivery. For this reason, capsules have been prepared by creating a membrane on the surface of the alginate bead. Most commonly, the membrane has been formed from the polycation poly-L-lysine, but chitosan (also a polycation) has also been used. In this way, a polycationic barrier is formed around the alginate gel which provides added stability and which can be effective in controlling parameters, such as pore size and the rate of drug release in sustained drug delivery.

Capsules of the above general type, methods of making them and their uses are known in the art and are described in, for example, the following patents:

U.S. Pat. No. 4,352,883 discloses a basic process for encapsulating a core material, such as a viable cell, within capsules having semipermeable membranes. This process comprises suspending the core material in a solution of a water-soluble polyanionic polymer capable of being gelled (especially an alginate salt), forming droplets which are then suspended in a solution of a polyvalent cation, such as $Ca^{2+}$, and thereby producing soft, shape-retaining, hydrated gelled masses. Thereafter, a membrane is formed about each of these gelled masses by reaction of the anionic groups from the polyanionic polymer hydrogel with cationic groups from a polycationic polymer. Useful polymeric cations include proteins and aminated polysaccharides or aminated polymers. The most preferred polycationic of this reference is polylysine.

Porosity control is an important factor in a number of important uses of such capsules. For example, the capsule membrane can be used for differential screening to separate molecules on a weight basis. U.S. Pat. No. 4,409,331 discloses a method of differential screening wherein lower molecular weight molecules secreted by a cell within the capsule core may traverse the capsule membrane while other higher molecular weight molecules are confined within the capsule. This is achieved through control of permeability within limits by selecting the molecular weight of the cross-linking polymer used and by regulating the concentration of the polymer solution and the duration of exposure. In general, the higher the molecular weight of the polymer solution and the less penetration, the larger the pore size.

In U.S. Pat. No. 4,690,682 it is further disclosed that release of the core material may be achieved through reliquifying the intracapsular volume by immersing the capsule in a solution of a sequestering agent that will remove the multivalent gelforming ions from the network. In this case, only the pore size of the membrane will have a determining effect on the sustained release properties of the capsule. However, in order to sustain the necessary osmotic gradient, a very large reservoir of core material must be maintained within the capsule and the core material which is released must be removed from the exterior of the capsule at a relatively rapid rate.

From U.S. Pat. No. 4,749,620, it is known to prepare polymer complex capsules having a liquid core through the direct formation of capsules from two solutions of polymers, where a polyanionic polymer solution is added dropwise to a polycationic polymer solution or vice versa. This is the so-called "one-step" process. Unfortunately, capsules having a liquid core show a lack of strength, which may make them unacceptable especially in uses where a certain capsule life time is necessary.

From U.S. Pat. No. 4,663,286 it is known to improve membrane uniformity and porosity control by expanding the gelled alginate beads in a saline bath essentially free from polyvalent cations, to remove some of the polyvalent cations from the alginate and further hydrate said gelled masses, and finally to form a membrane about the hydrated gelled masses to form capsules by reaction between the anionic groups on the alkali metal alginate and cationic groups on a polycationic polymer. Optionally, further membrane layers can be formed by either coating the membrane layer with an anionic polymer or a cationic polymer.

While poly-L-lysine (hereinafter polylysine) has most commonly been used for the formation of the membrane layer of the capsules, it has particular disadvantages in use. Thus, polylysine is known to be an irritant which makes it less suitable for use in pharmaceutical preparations, more especially for preparations intended for use in easily irritated areas such as the throat or stomach. Also, it has been suggested that polylysine can be enzymatically degraded which in some applications will reduce unacceptably the life time of the capsule. The prior art has addressed this problem by adding further layers of polyanionic or polycationic polymers, but this is expensive and cumbersome. It may also be noted the polylysine itself is an expensive synthetic protein.

As an alternative to polylysine, chitosan has been proposed because it is a natural, non-toxic, biodegradable polymer already known as a natural component in many consumer food products and is also cheaper than polylysine. Chitosan is a partially de-acetylated chitin, which is one of the most common biopolymers in nature and which appears in many organisms as a structural component. Through the deacetylation of chitin (which is insoluble) chitosan may be produced which is soluble in acidic solutions. Commercially available chitosans generally contain about 75 to 95% glucosamine units and about 5 to 25% N-acetylglucosamine units connected through (1–4) linked β-glycosidic linkages. Through the amino groups, chitosan may be protonated with the result that chitosan is one of the few biopolymers which are cations at physiological pH.

However, chitosan has not found acceptance because capsules prepared by the addition of cross-linked polyanionic (e.g. alginate) beads to a chitosan solution have been found to have insufficient strength. This is because it has been possible to provide only a small, thin layer of the chitosan on the polyanionic polymer (e.g. alginate) bead. Commercially available chitosans which have been used in prior art capsules have had a high molecular weight of 100,000 or more. The reaction time required to form a layer of chitosan on an alginate bead is also considerably longer than the time required to provide a corresponding polylysine layer.

In view of the above, the present invention seeks to provide a method of preparing polyanion-polycation (e.g. alginate-chitosan) capsules of higher strength.

SUMMARY OF THE INVENTION

It has now surprisingly been found that higher strength capsules of the type having a polyanionic polysaccharide core and a polycationic polysaccharide membrane can be formed by adding or providing a polyvalent ion, such as $Ca^{2+}$, in the polyanion-polycation membrane forming step.

Accordingly, a first aspect of the present invention provides a process for preparing high strength capsules comprising the steps of:

(a) preparing gelled beads of a polyanionic polysaccharide which are cross-linked with a polyvalent cation, (b) forming capsules having a polycation-polyanion membrane layer on the gelled beads by adding the beads to a solution comprising a polycationic polysaccharide, (c) optionally forming one or more additional polycationic or polyanionic layers on the capsules, and (d) harvesting the resulting capsules, characterised in that the process further includes the step of (e) providing a polyvalent cation in the polycationic polysaccharide solution of step(b).

In a first embodiment of this aspect of the invention, step (a) comprises:

(i) providing a first solution comprising the polyanionic polysaccharide, (ii) providing a second solution comprising the cross-linking polyvalent ions and a non-gelling ion, preferably sodium ions, and (iii) adding the first solution in drops to the second solution, thereby to prepare homogeneous capsules.

In a second embodiment of this aspect of the is invention, the process of the invention further comprises providing a solution of a non-gelling ion, preferably sodium ions, and immersing the beads of step (a) in the solution of non-gelling ion, thereby to prepare homogeneous capsules.

In other preferred embodiments of this aspect of the invention, the process further comprises including an active ingredient, material or substance in the gelled bead of step (a). The active ingredient material or substance may advantageously be encapsulated in the gelled bead.

In a further embodiment of this aspect of the invention, the polyvalent cation in the membrane forming step (step (e)) is present at a concentration of from 50 mM to 400 mM, preferably 100 mM to 300 mM.

In preferred variations of the first and second embodiments of this aspect of the invention, the non-gelling ion is present at a concentration of at least 10 mM, more preferably 100 mM to 300 mM.

In another preferred variation of the first and second embodiments of this aspect of the invention, the membrane forming step (step (b)) proceeds for at least 15 minutes, preferably 2 to 5 hours, more preferably 30 minutes to 1 hour. Where a non-gelling ion is not employed, the membrane forming step (step (b)) preferably proceeds for at least 30 minutes, more preferably 2 to 5 hours and especially 1 to 2 hours.

A second aspect of the invention provides capsules obtainable by the process of the first aspect of the invention.

In preferred embodiments of this second aspect of the invention, the capsules contain a pharmaceutically active ingredient or composition. In further preferred embodiments of this aspect of the invention, the pharmaceutically active ingredient is selected from acid neutralising agents, local anaesthetics, histamine $H_2$-receptor antagonists and antimicrobial agents.

Further aspects of the invention comprise the use of the capsules of the second aspect in therapy, more especially in the treatment of one or more of gastro-oesophageal reflux, sore throat, dyspepsia and/or heartburn, and *Heliobacter pylori* infections.

Additional aspects of the invention comprise the use of the capsules of the second aspect in the preparation of a medicament for the treatment of one or more of gastro-oesophageal reflux, sore throat, dyspepsia and/or heartburn, and *Heliobacter pylori* infections.

DETAILED DESCRIPTION OF THE INVENTION

In further preferred embodiments of the invention, the polyanionic polysaccharide is an alginate, but any other polyanionic polysaccharide with can be cross-linked and/or is gellable by means of a polyvalent cation may be used, of which pectin is an example. The inventors have found that further improved chitosan binding is achieved when the alginate bead core has a higher G-block content. Accordingly, preferred alginates have a G-block content of at least 50%, more preferably 60 to 75%.

Also in preferred embodiments of the invention, the polycationic polysaccharide is chitosan. However, any other polycationic polysaccharide which is capable of interaction with the polyanionic polysaccharide may be used. Suitable examples are polycationic polysaccharides carrying an amino group or an imine group, of which diethylaminoethyl dextran (DEAE Dextran) may be specifically mentioned.

Preferably, the polyvalent cation in step (e) is selected from calcium, strontium, barium, aluminium (III) or iron (III), and is most preferably calcium. In particular applications, other polyvalent ions such as nickel, lead or copper may be used, although these latter ions may also not be suitable in some uses because of possible toxic or allergenic effects.

Through the addition of a polyvalent cation to the polyanion-polycation membrane forming step according to the present invention, more of the polycationic polysaccharide can be bound to the polyanionic polysaccharide bead, whereby higher strength capsules result. Without wishing to be bound by theory, the inventors suggest that the improved binding of the polycationic polysaccharide to the polyanionic polysaccharide bead in the present invention may be attributable to the effect of the added polyvalent cation on the pore structure of the polyanionic polysaccharide gel. Thus, the added polyvalent cation may provide a further alignment of the polyanionic polysaccharide polymer chains in the gelled bead so that the existing pore network is further defined or even enlarged. In this way, a more open network results which the polycationic polysaccharide is better able to penetrate and which thus enhances the anion-cation interactions of the polyanionic polysaccharide and the polycationic polysaccharide.

The polycationic or polyanionic polymers used in the optional additional membrane layers in step (c) above may be the same as or different from those used to prepare the gelled bead in step (a) or the first membrane layer of step (b). Examples of alternative polymers include pectin, acacia, sterculia, carrageenan and polylactic acid. Examples of alternative polycationic polymers include dermatan and chondroitin.

An active ingredient, material or substance can advantageously be provided in the polyanionic polysaccharide core of the capsules prepared according to the invention, and may be encapsulated by or dispersed in the core, depending on its nature and purpose. Any active ingredient, material or substance may in principle be included, in particular pharmaceutically active drugs, catalysts, living or dead cells, tissue, agriculturally useful substances such as pesticides, herbicides, nutrients and fertilisers or seeds, cosmetic products and food ingredients. In some applications, the capsules prepared in accordance with the invention need not include any active ingredient at all, or may include only additives providing a desired colour or taste, or sweeteners or the like.

Through the variation of additional parameters, such as the molecular weight of the polycationic polysaccharide, the relative content of G-blocks, if alginate is used as the polyanionic polysaccharide, the concentration of the polyvalent ion in the membrane forming step and the homogeneity of the polyanionic polysaccharide beads, it is possible to tailor the properties of the capsules prepared according the process of the invention. Thus, it is possible to control properties such as: the porosity of the polycationic polysaccharide membrane, the capsule size, the adherence of the capsules to different surfaces, and, if an active ingredient is included in the core of the capsule, the rate of release of said active ingredient.

When preparing capsules according to the invention for sustained release of a drug or other active ingredient, it is necessary to take into account the size (eg molecular size) of the active ingredient and the molecular weight of the polycationic polysaccharide. Generally, the addition of the polycationic polysaccharide membrane will reduce the porosity of the capsule as compared with that of the polyanionic polysaccharide bead and the capsule porosity will be dependant on the molecular weight of the polycationic polysaccharide. Increasing molecular weights of the polycationic polysaccharide will in general provide a lower porosity. Thus, for example, alginate-chitosan capsules wherein the chitosan has a low molecular weight in the range of from about 5000 to about 30,000 will have a relatively open pore structure and consequently a higher rate of release of active ingredient. Capsules wherein the chitosan has a relatively higher molecular weight, for example about 60,000 or more, will tend to have a reduced pore size and a lower rate of release of active ingredient.

The molecular weight of the polycationic polysaccharide also has an effect on the strength of the capsules according to the invention. In the case of chitosan, a molecular weight of about 60,000 or more, preferably about 60,000 to about 100,000 results in a relatively thin chitosan membrane layer whereas a chitosan molecular weight in the range of from about 5,000 to about 60,000 provides increasingly thicker membrane layers with decreasing molecular weight. Relatively thicker chitosan membrane layers provide higher strength capsules and, in this respects it is preferred to use chitosans having a molecular weight in the range of from about 10,000 to about 30,000.

The thickness of the polycationic polysaccharide membrane layer can also be selected in accordance with the desired end use of the capsule. For example, capsules according to the invention can be used to mask the taste of unpleasant tasting drugs, in which case a capsule having only a thin chitosan layer is suitable. In contrast, where adhesion of the capsule to a particular site of action, such as a body surface, is required, a thicker chitosan membrane layer may be desirable.

Where the capsules of the invention are used for drug release, blends of capsules with different membrane layers and/or different membrane thickness may be used to provide a pulsed release of the drug.

The size of the capsules according to the invention may also affect the capsule strength. Preferably the capsule has a diameter of from about 0.1 mm to about 1.0 mm, preferably about 0.2 mm to about 0.7 mm. Capsules having a diameter of from about 0.3 mm to about 0.4 mm are especially preferred where high strength is required.

A particular advantage of the capsules prepared according to the process of the invention, and more especially of such capsules where the polycationic polysaccharide is chitosan, is that the capsules adhere well to negatively charged surfaces. As most body tissue is negatively charged, the polycationic polysaccharide (e.g. chitosan) membrane layer in the capsules of the invention allows the capsules to adhere to and be retained at suitable body locations by means of polyanion-polycation interactions. In particular, the capsules can adhere to mucous membrane surfaces such as those of the gastro-intestinal tract. Capsules having a homogeneous polyanionic polysaccharide core are particularly advantageous in this respect. The ability of the capsules of the invention to adhere to body surfaces is especially beneficial in achieving enhanced drug delivery to the body. Because the capsules adhere well to body tissues, drugs contained in the capsules can be delivered to the body in a sustained and/or targeted manner.

The capsules of the invention may be prepared by the following general method:

i) prepare a 2% w/v solution of alginate; salt (usually sodium alginate)

ii) add the alginate salt solution dropwise into a 50 mM calcium chloride solution; where homogeneous capsules are required, the solution may also include sodium chloride (200 mM).

iii) collect the uncoated alginate beads and stir into a 0.15–0.3% w/v solution of chitosan chloride also containing 300 mM calcium chloride in a 0.02 M sodium acetate/acetic acid buffer;

iv) collect and, if required, concentrate the beads.

An exemplary method of adding the alginate salt solution dropwise to the calcium chloride is as follows:

To prepare beads having a diameter of 500 $\mu$m, drops of alginate salt solution were allowed to fall from a steel needle having a diameter of 0.4 mm into a gelling bath of calcium chloride solution. An electrostatic charge of 7 kV was connected between the needle and the gelling solution, with the voltage coupled to the gelling bath and the needle coupled to earth. The distance between the needle tip and the gelling bath was maintained at 10 mm and the alginate salt solution was fed to the needle by means of a syringe pump at a flow rate of 30 ml/hour. The diameter of the beads was calculated as the average of 20 beads using a Nikon Inverted Microscope (Diaphot-TMD) and the standard deviation of the bead diameters was found to be 3–6% relative to the average.

It will be appreciated that in the above methods, various parameters such as concentrations, needle diameter, dropping rate may be varied in order to tailor the properties and characteristics of the resulting capsules.

BRIEF DESCRIPTION OF THE DRAWINGS

For a better understanding of the invention, reference will now be made to the following Figures, in which:

FIG. 14 illustrates the rate of release of haemoglobin from alginate-chitosan capsules for different chitosan molecular weights and for homogeneous and inhomogeneous alginate capsule cores;

Referring now to FIGS. 1 and 2 it can be seen from FIG. 1 that with increasing $CaCl_2$ concentration there is a surprising and significant increase in the amount of chitosan which binds to the alginate bead to form the membrane layer, over a period of 24 hours. FIG. 2 illustrates that although there is an increase with increasing NaCl concentration in the amount of chitosan which binds to the alginate bead, the increase is significantly less than that achieved with $CaCl_2$. This suggests that the increase in chitosan binding efficiency which occurs with increasing $CaCl_2$ concentration cannot simply be attributable to increasing ionic strength of the chitosan solution in which the binding reaction occurs.

Figure 1:
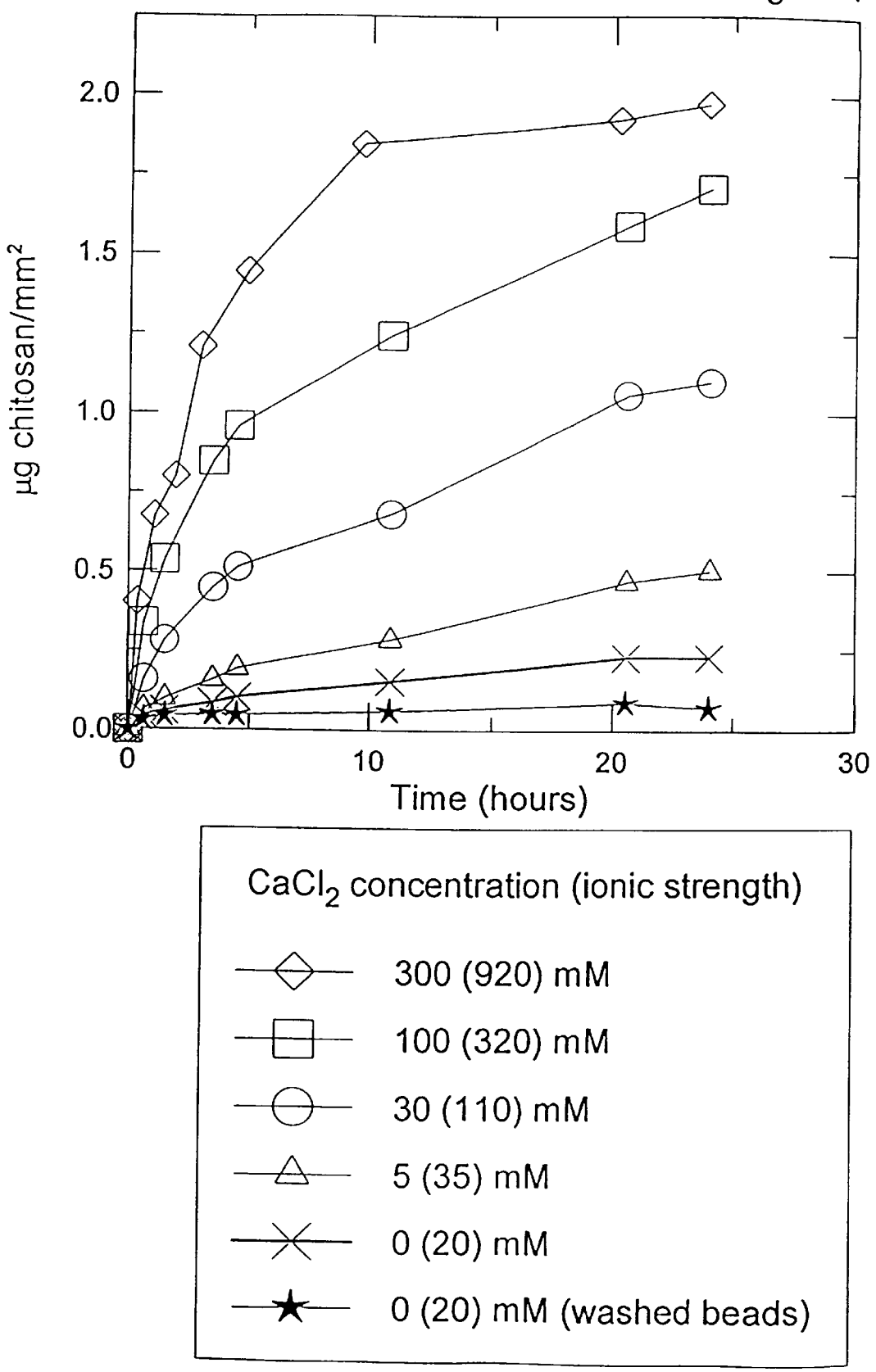
FIG. 1 shows the degree of chitosan binding to inhomogeneous alginate beads in the presence of different amounts of $CaCl_2$.
Figure 2:
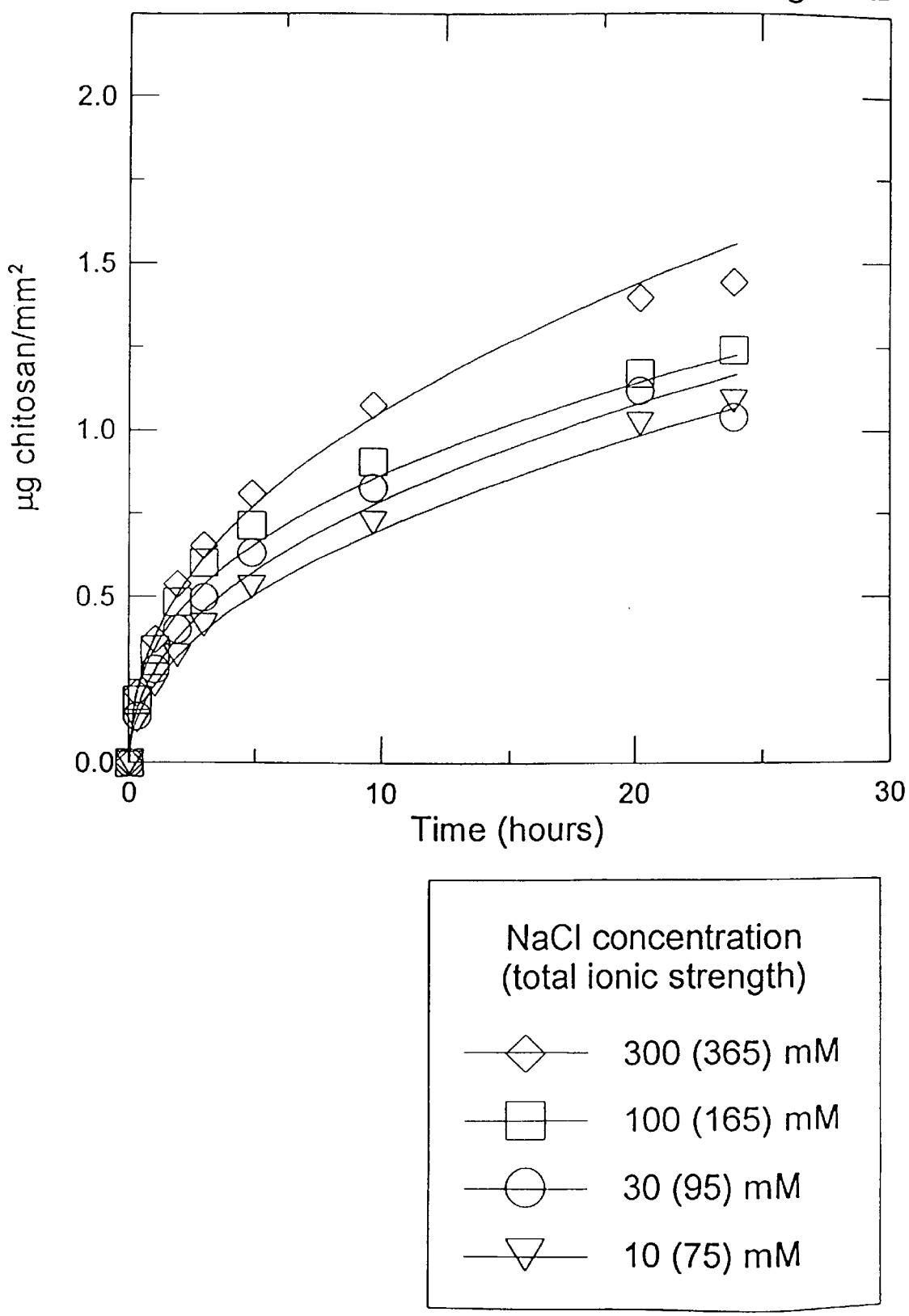
FIG. 2 shows the degree of chitosan binding to inhomogeneous alginate beads in the presence of different amounts of NaCl (and 15 mM $CaCl_2$ in order to prevent swelling of the capsules)
Figure 3:
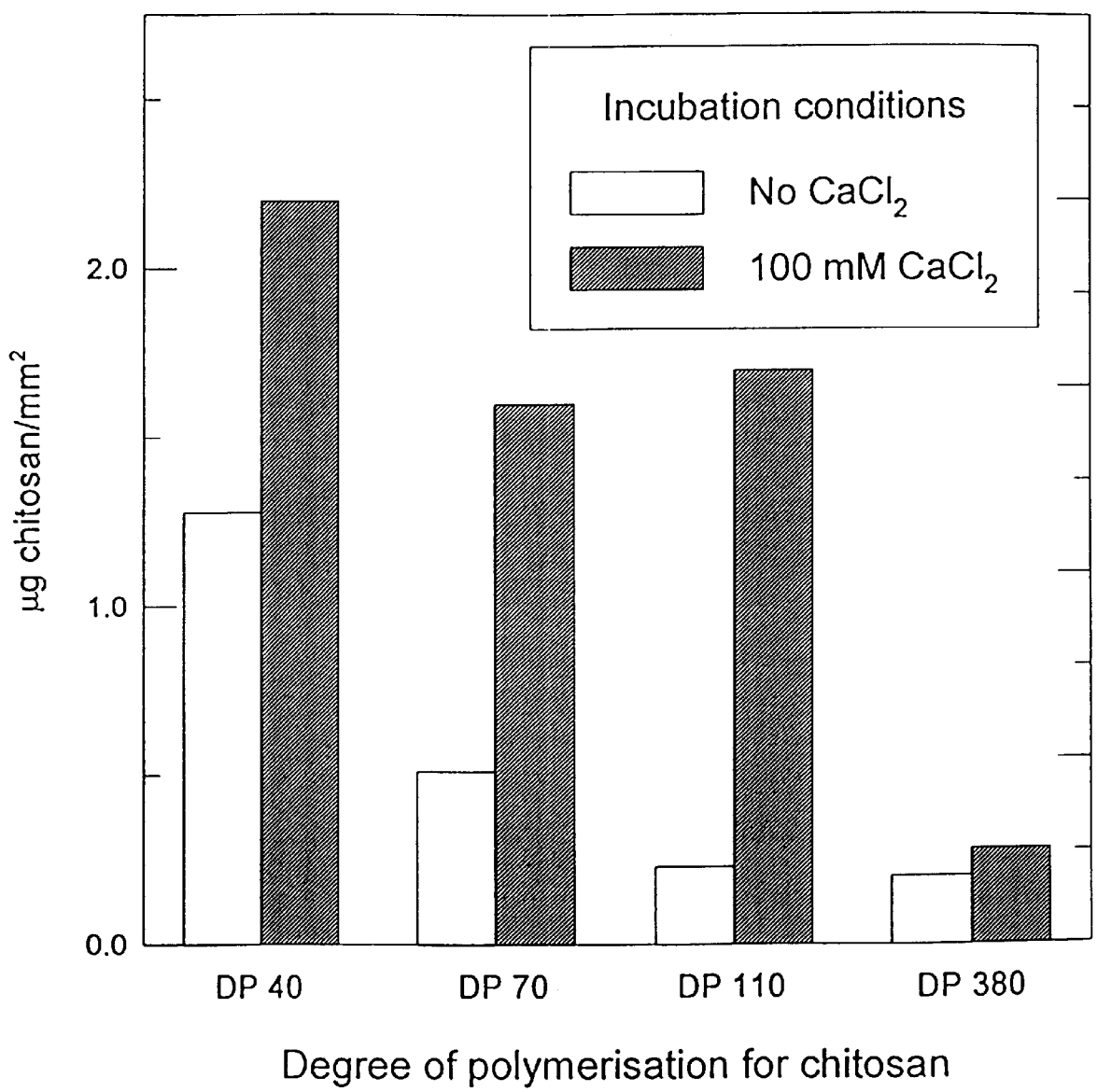
FIG. 3 shows the degree of chitosan binding to alginate beads at concentrations of $CaCl_2$ of 0 and 100 mM and for various chitosan molecular weights (expressed as Degree of Polymerisation (DP))

From FIG. 3 it is apparent that the increasing binding efficiency of chitosan in the presence of $CaCl_2$ occurs for a range of molecular weights of chitosan, with a particularly large increase occurring for chitosan having a degree of polymerisation (DP) of about 110, and below.

Figure 4:
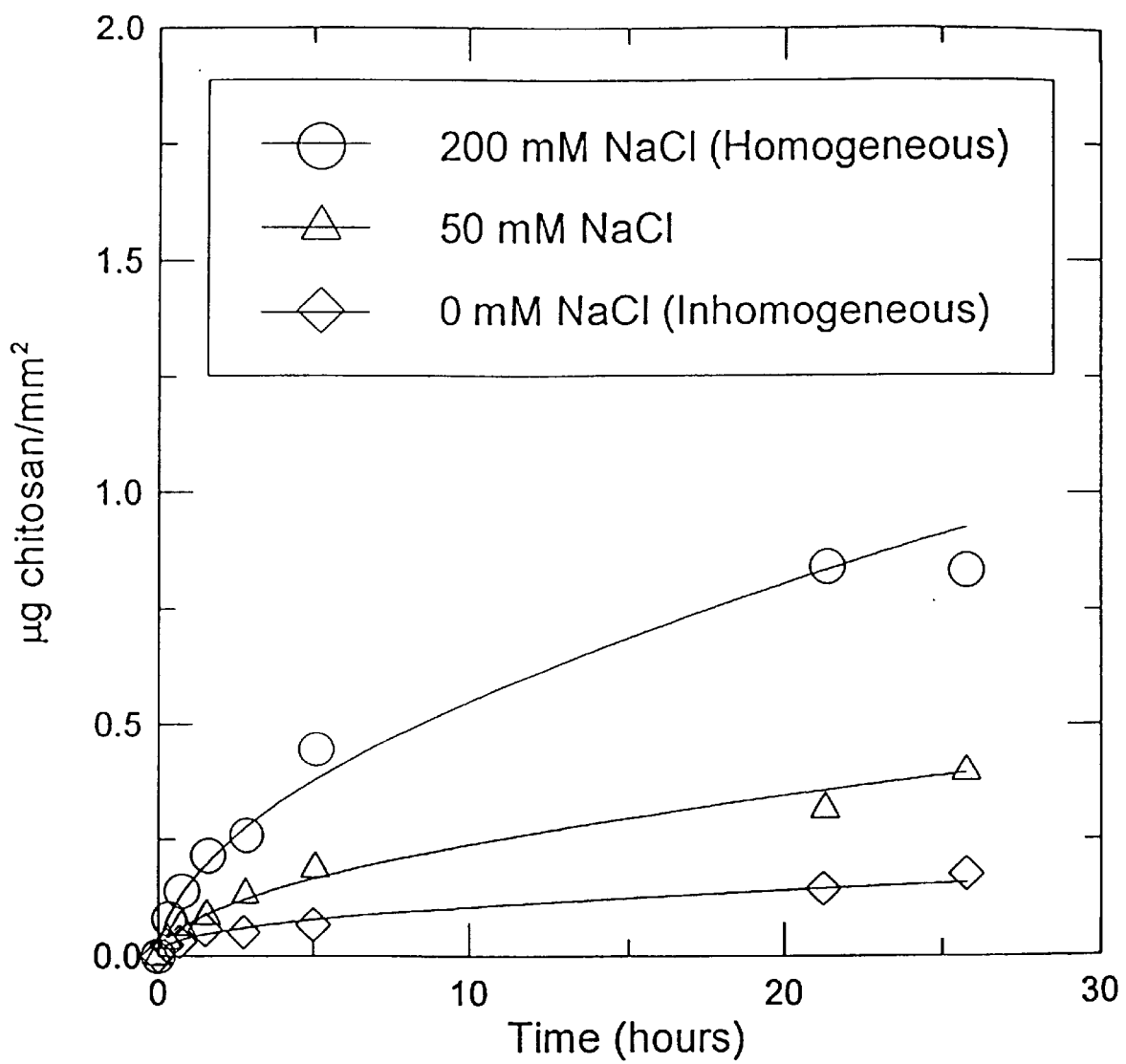
FIG. 4 shows the degree of chitosan binding to alginate beads with different homogeneity.
Figure 5:
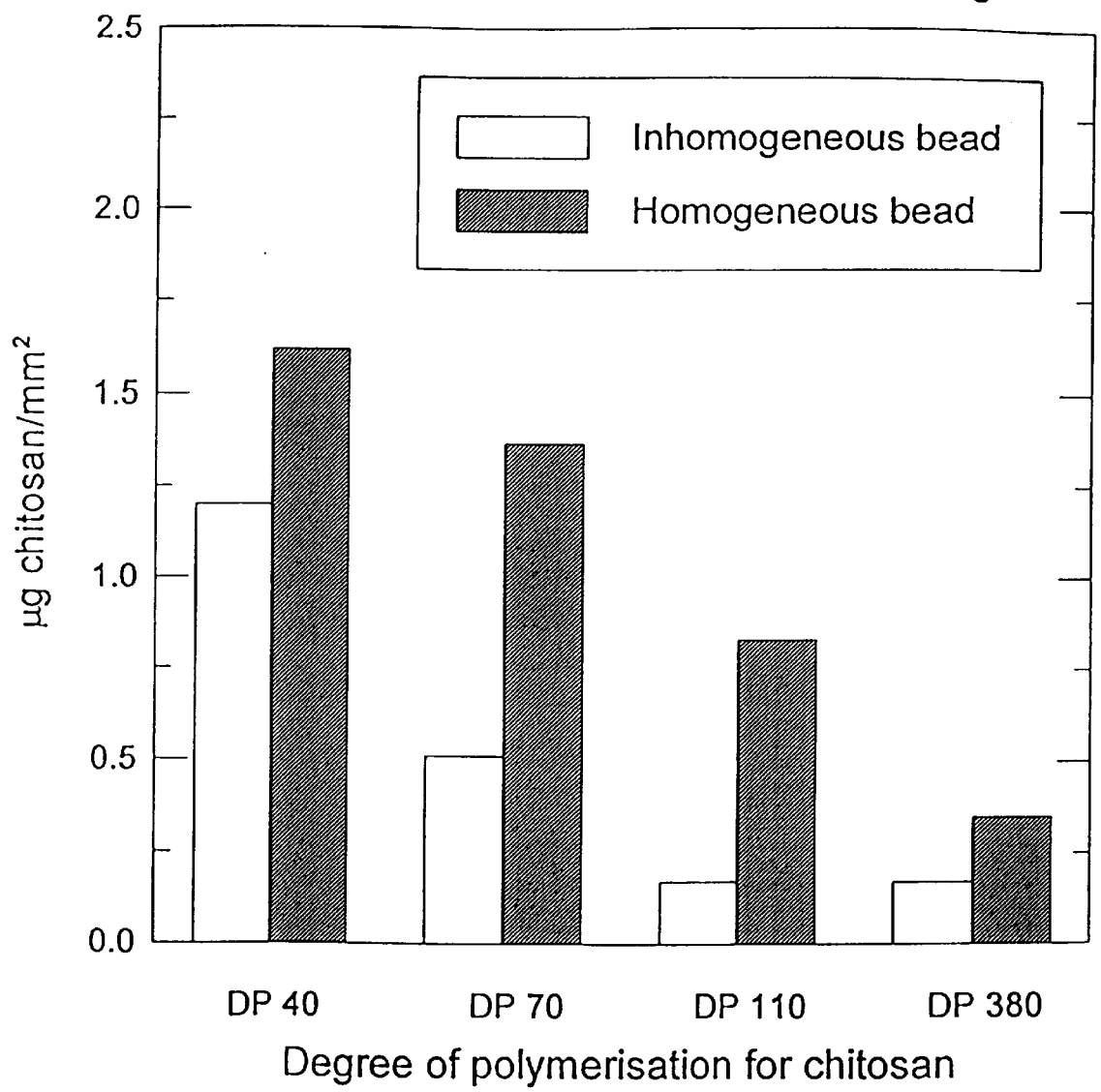
FIG. 5 shows the degree of chitosan binding to homogeneous and inhomogeneous alginate beads for different chitosan molecular weights (DP)

FIG. 4 illustrates the relative increase in binding efficiency of chitosan on homogeneous and inhomogeneous alginate beads in the presence of $CaCl_2$, and demonstrates that a further improved degree of chitosan binding can be achieved with homogeneous alginate beads. When gelling a drop of alginate solution by cross-linking with calcium ions in a $CaCl_2$ bath, the gelling reaction occurs at the interface between the alginate and $CaCl_2$ solutions and is controlled by diffusion of the alginate chains towards the interface and diffusion of calcium ions across the interface and into the alginate solution. The resulting alginate gel therefore has an inhomogeneous structure with respect to the alginate concentration across a cross-section of the bead, with the highest alginate concentration tending to be towards the surface of the bead. More homogeneous alginate gel beads can be prepared by including sodium chloride in the cross-linking polyvalent cation solution at the initial bead-forming step. In FIG. 4 an increasing NaCl concentration indicates an increasing degree of homogeneity. Thus, in a homogeneous alginate bead there is substantially no alginate concentration gradient through the bead cross-section whereas in an inhomogeneous alginate bead, the alginate concentration at the surface of the bead can be at least five times that at the centre. The increased degree of chitosan binding to homogeneous alginate beads is further illustrated in FIG. 5 for a range of chitosan molecular weights (expressed as degree of polymerisation).

FIGS. 6 to 12 show the results of explosion assays of capsules according to the invention, illustrating the strength of the capsules for various parameters.

In these explosion assays, about 100 capsules were kept for 15 minutes in 0.15 M NaCl solution. The capsules were then transferred to deionised water which results in an increase in the osmotic pressure inside the capsules. The proportion of unbroken capsules over time was measured by counting the capsules using the microscope as described above in relation to the bead preparation method.

Figure 6:
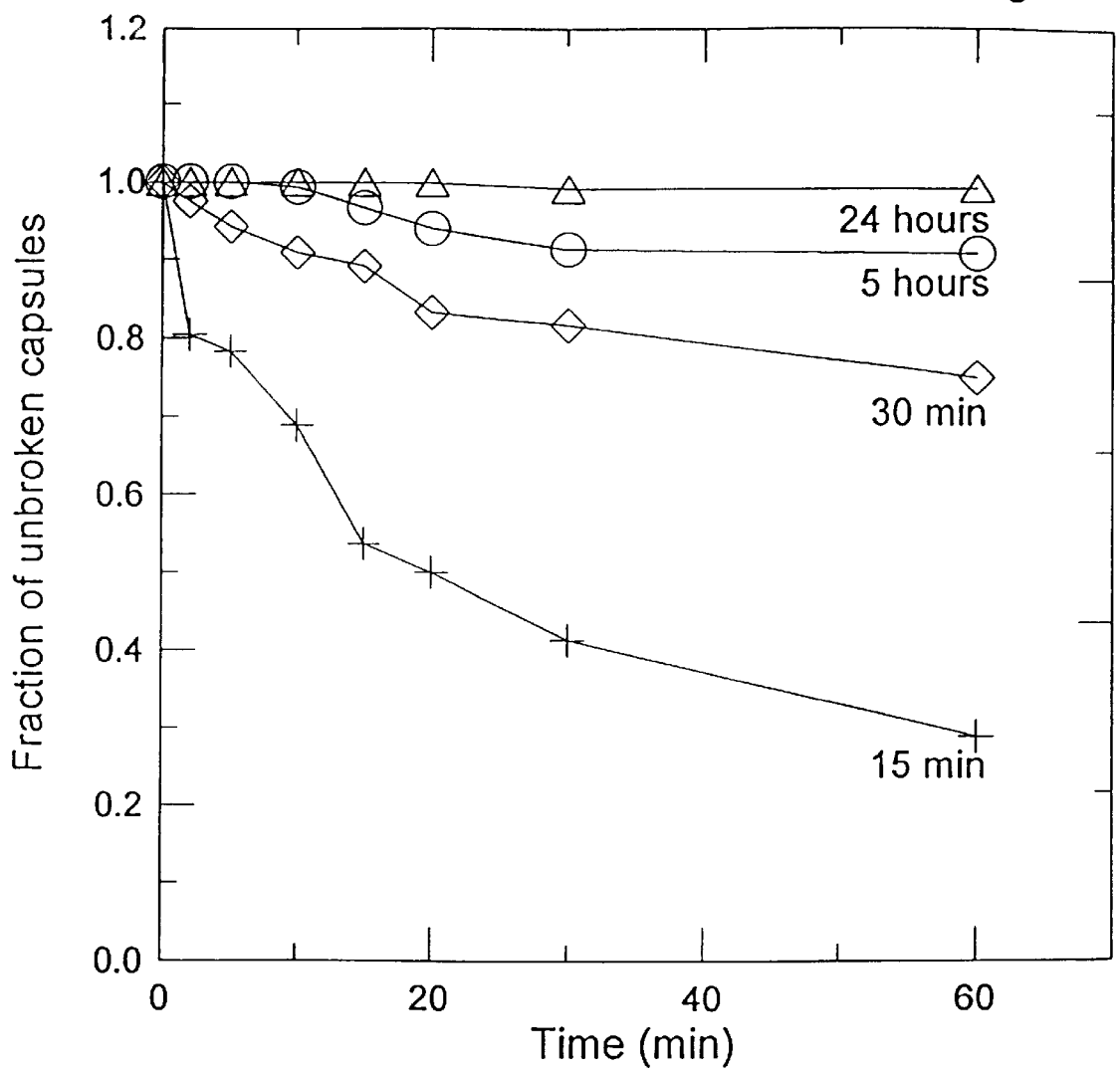
FIG. 6 shows the results of an explosion assay of alginate-chitosan capsules having an inhomogeneous alginate core and for different alginate-chitosan reaction times.
Figure 7:
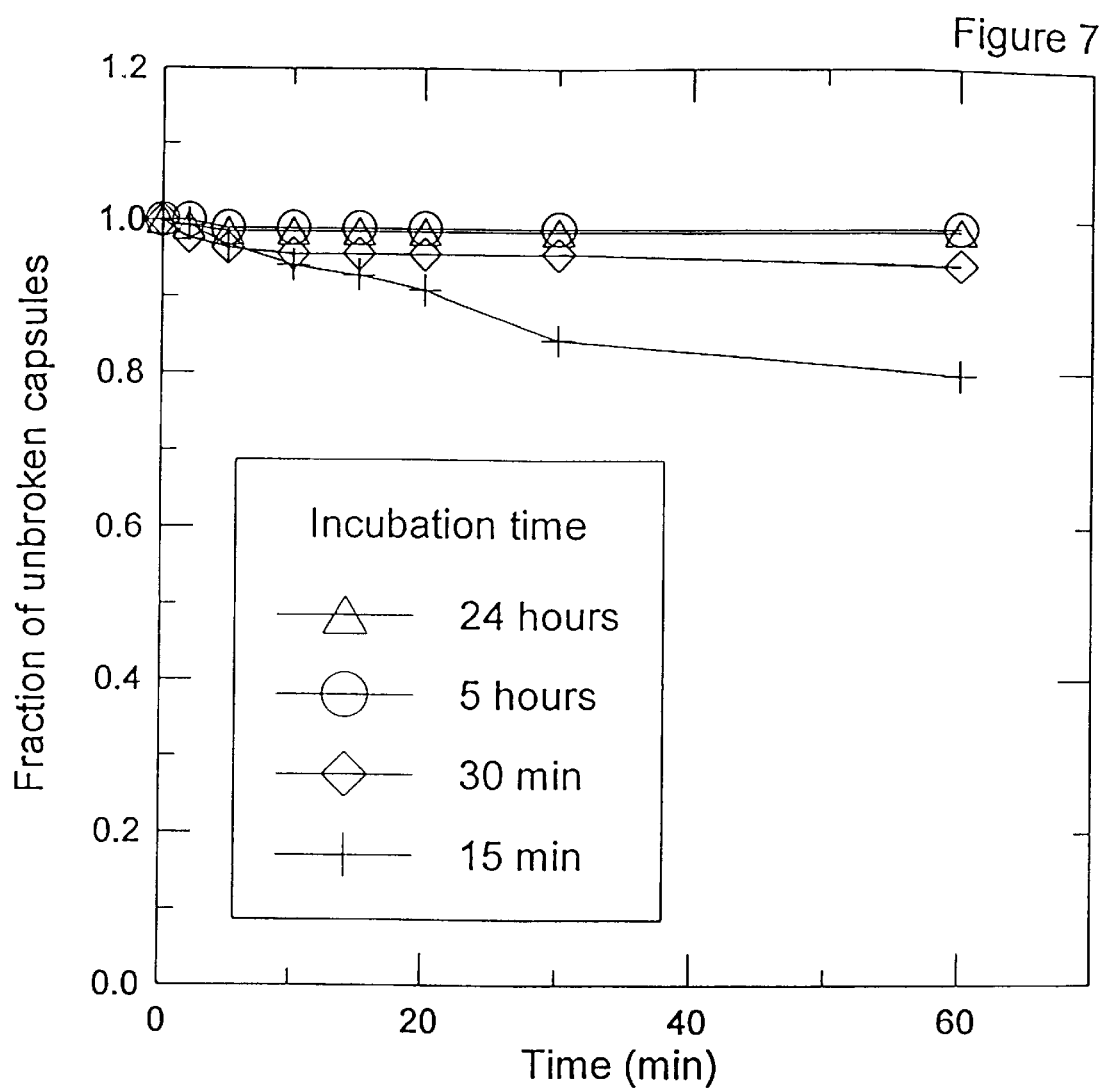
FIG. 7 shows the results of an explosion assay of alginate-chitosan capsules having a homogeneous alginate core and for different alginate-chitosan reaction times.

FIG. 6 illustrates capsules having an inhomogeneous alginate core for incubation times of the alginate beads in a chitosan/$CaCl_2$ bath of from 15 minutes to 24 hours. It can be seen that stronger capsules are formed with an incubation time of at least 30 minutes and more preferably two hours or more. FIG. 7 demonstrates the effect of incubation time of homogeneous alginate beads in the chitosan/$CaCl_2$ bath and shows that higher strength capsules can be formed with shorter reaction times than is required for inhomogeneous alginate beads.

Figure 8:
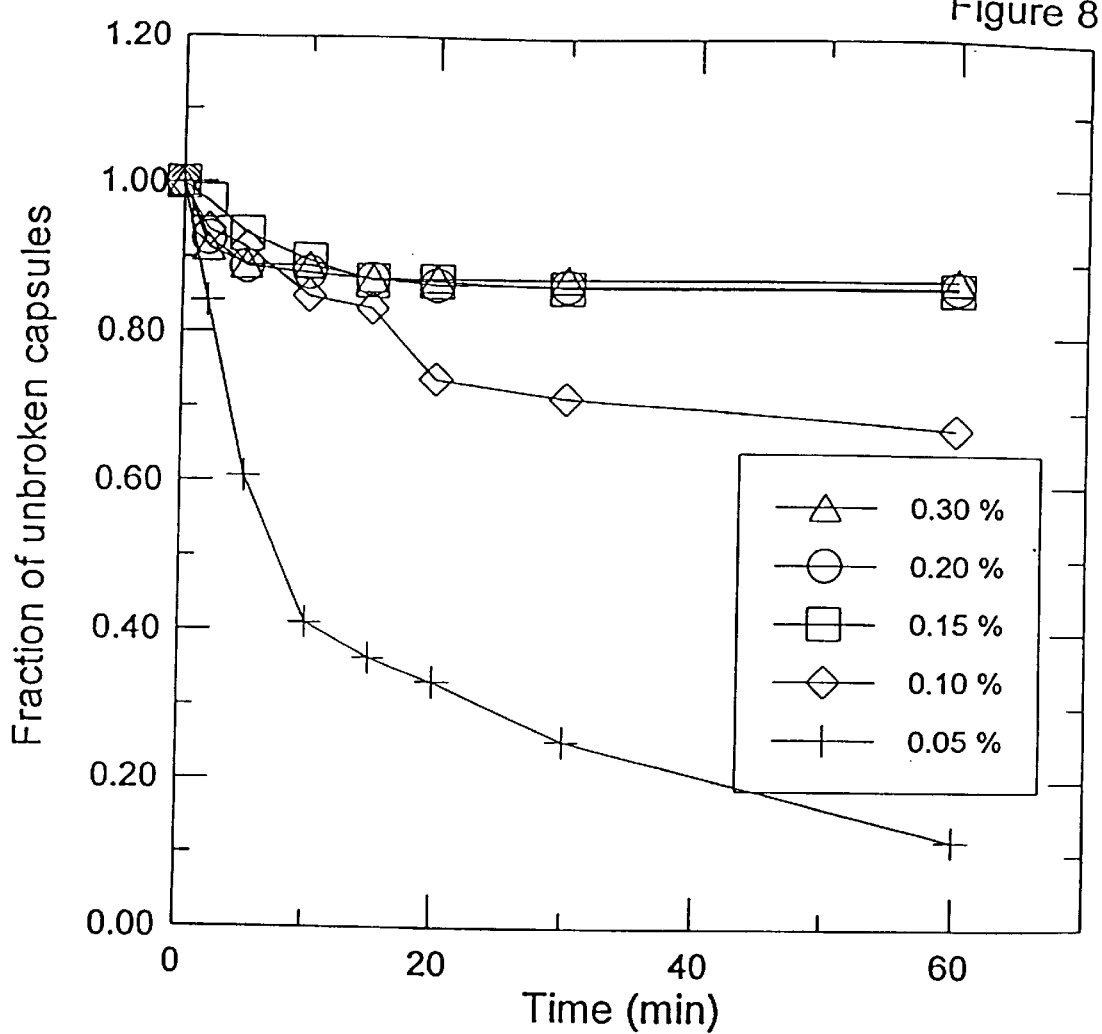
FIG. 8 illustrates the strength of alginate-chitosan capsules for different chitosan concentrations.

FIG. 8 shows the variation of capsule strength with the concentration of chitosan in the chitosan/$CaCl_2$ bath. A chitosan concentration of at least 0.10% is preferable in order to obtain high strength capsules.

Figure 9:
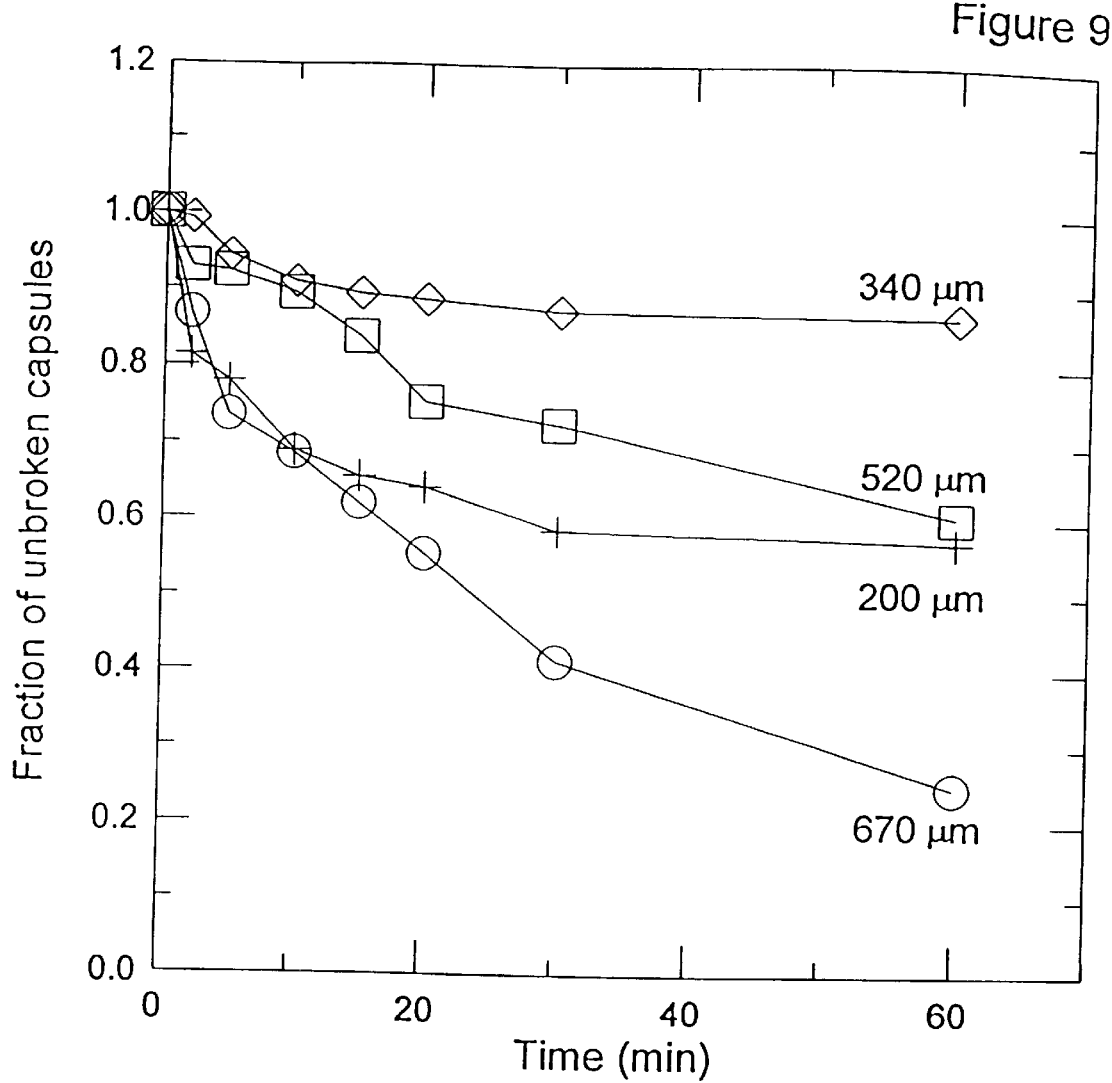
FIG. 9 illustrates the influence of capsule size on capsule strength for a short alginate-chitosan reaction time of 30 minutes.
Figure 10:
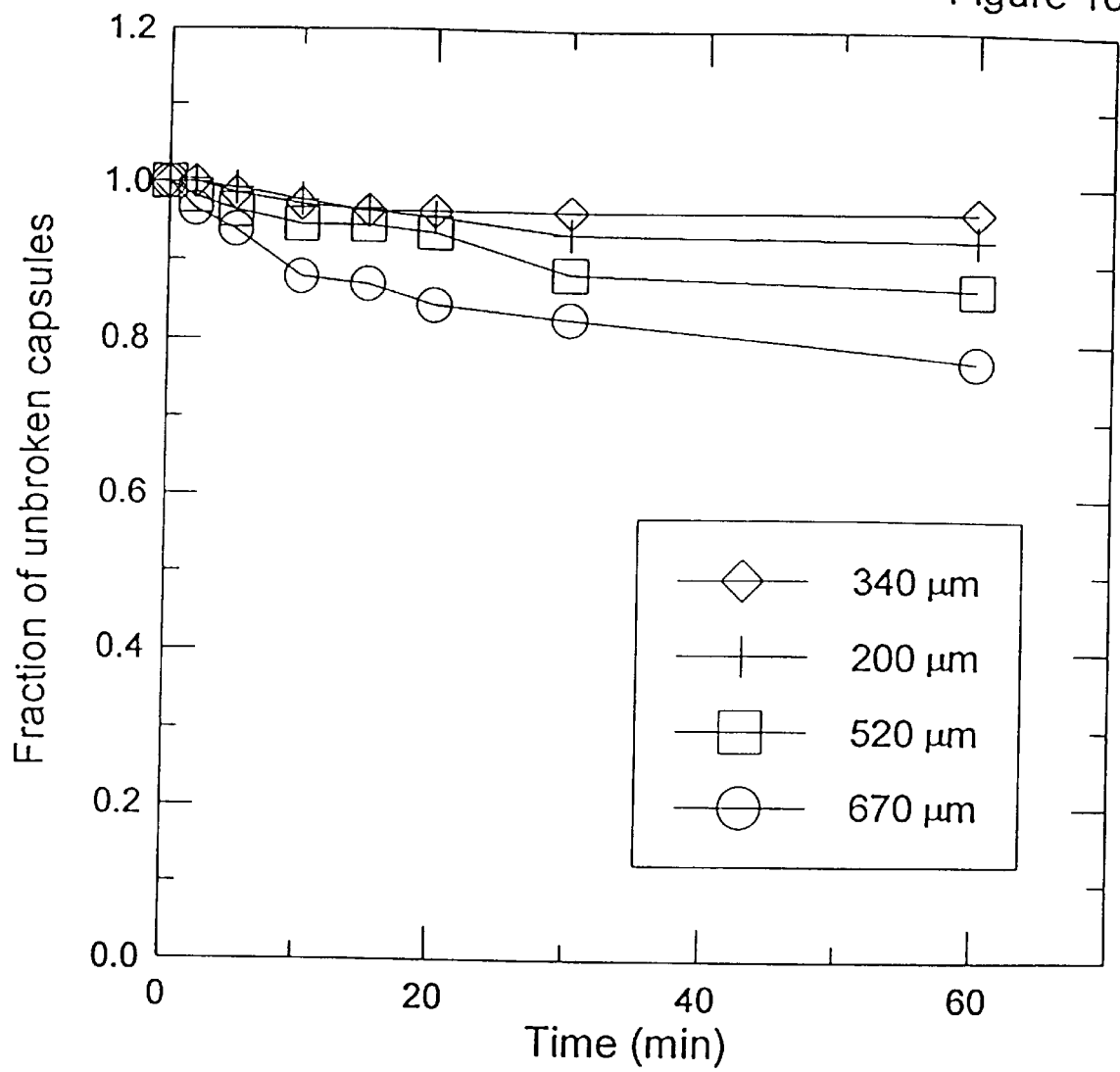
FIG. 10 is similar to FIG. 9, but for an alginate-chitosan reaction time of 2 hours and for homogeneous capsules.

The dependence of the capsule strength on the size of the capsule is shown in FIG. 9, for inhomogeneous capsules having a short incubation time in the chitosan/$CaCl_2$ bath of 30 minutes. Of the capsule sizes tested, capsules having a diameter of 0.34 mm were found to be optimal. FIG. 10 illustrates the improvement in capsule strength which can be achieved using homogeneous alginate beads and an incubation time in the chitosan/$CaCl_2$ bath of two hours.

Figure 11:
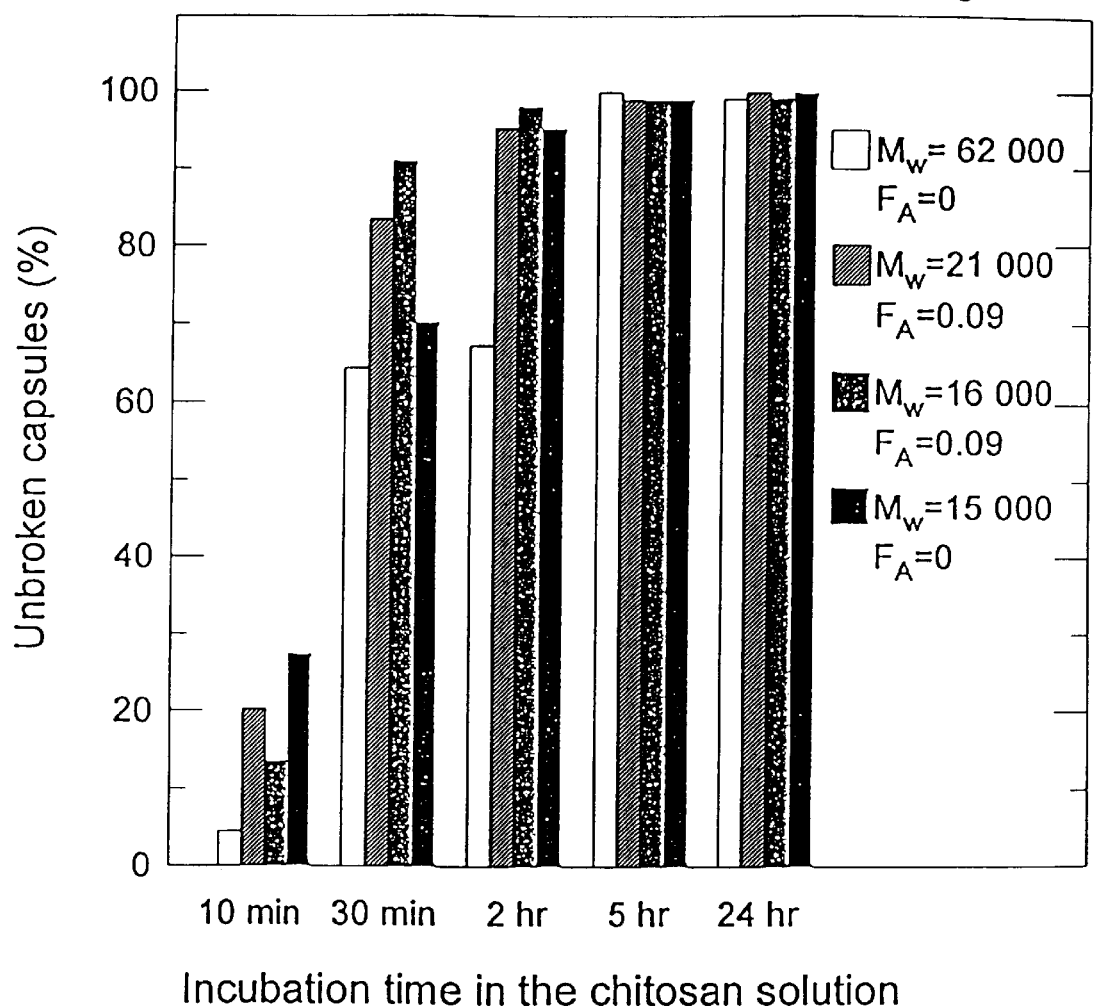
FIG. 11 illustrates the results of an explosion assay and shows the strength of capsules for different chitosan molecular weights and different alginate-chitosan reaction times.

In FIG. 11, the strength of capsules with various chitosan molecular weights and different incubation times in the chitosan bath is illustrated. It is apparent that an incubation time of 30 minutes or more is preferable and that for higher chitosan molecular weights of about 60,000, a longer reaction time is desirable in order to achieve higher strength capsules.

Figure 12:
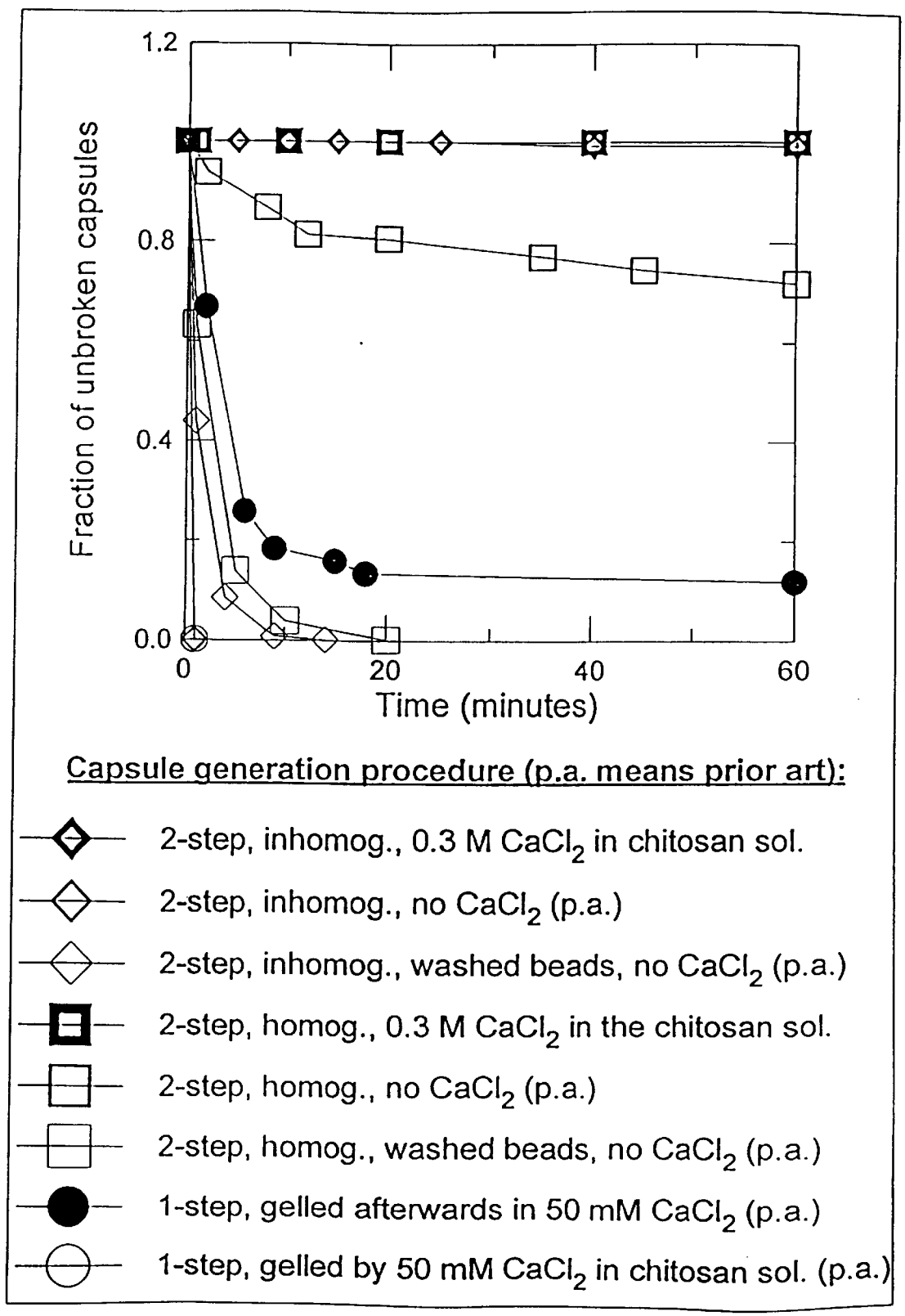
FIG. 12 shows a comparison of the strength of alginate-chitosan capsules of the present invention with those prepared by methods of the prior art.

FIG. 12 clearly illustrates the higher strength capsules obtainable by the process of the present invention as compared with the processes of the prior art, for homogeneous and inhomogeneous alginate cores. The prior art process including no addition of calcium ions to the chitosan bath, and the prior art one-step process of dropping alginate directly into the chitosan bath each produces capsules of inadequate strength. In the process of the invention, the step of adding calcium ions to the chitosan bath provides a remarkable increase in the capsule strength.

Figure 13:
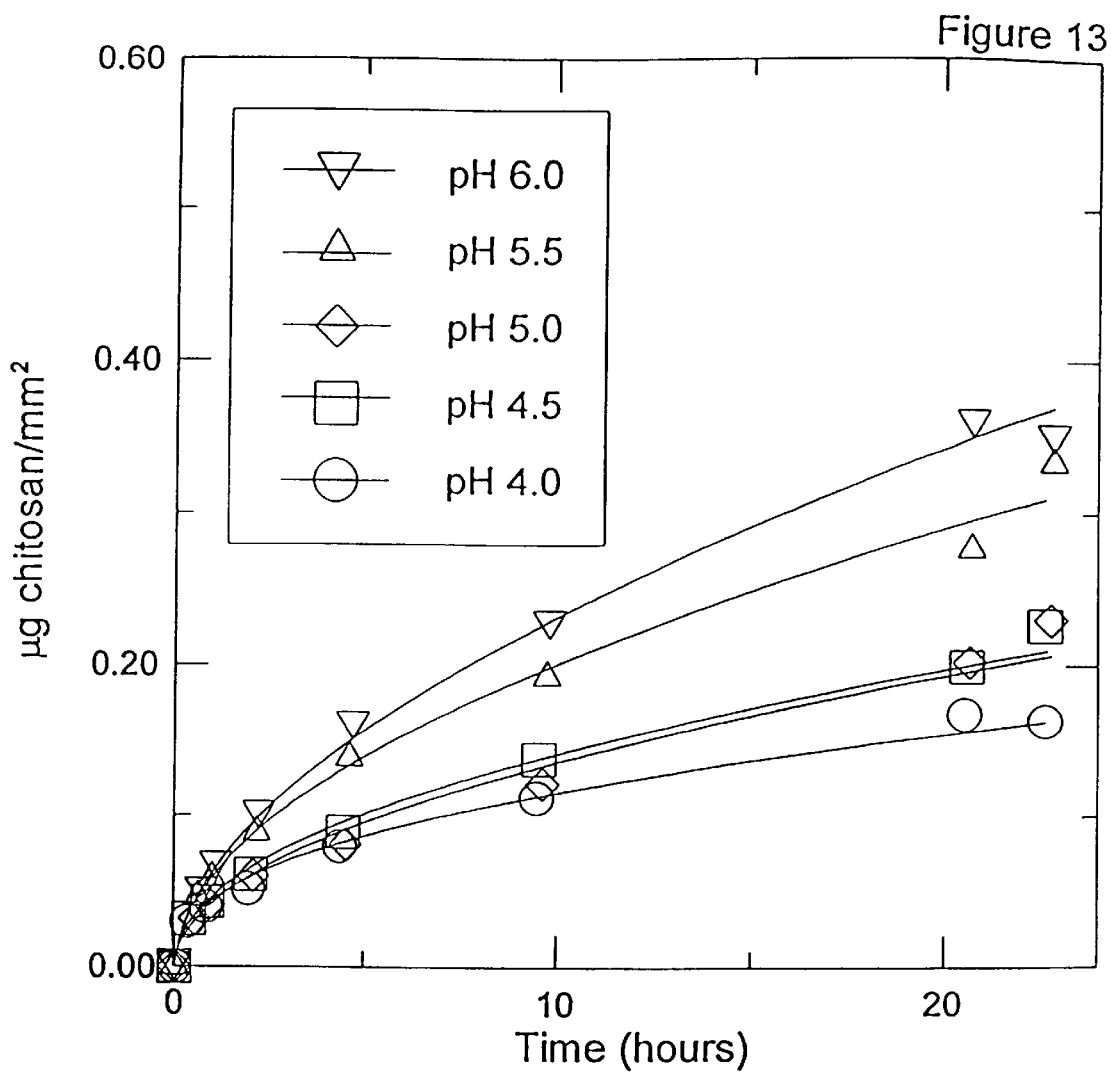
FIG. 13 shows the variation of the chitosan binding to inhomogeneous alginate beads as a function of pH.

FIG. 13 demonstrates that in the process of the invention, increased chitosan binding can be achieved at higher pH, in particular at pH 5 to pH 6. The alginate beads were incubated in the chitosan/$CaCl_2$ bath for 24 hours.

FIG. 14 illustrates how the rate of release of an active ingredient from the capsule can be controlled. Thus, different release rates can be achieved by varying the molecular weight of the chitosan used and by using homogeneous or inhomogeneous capsules. In the case of haemoglobin, higher release rates are achieved with lower chitosan molecular weights.

Figure 15:
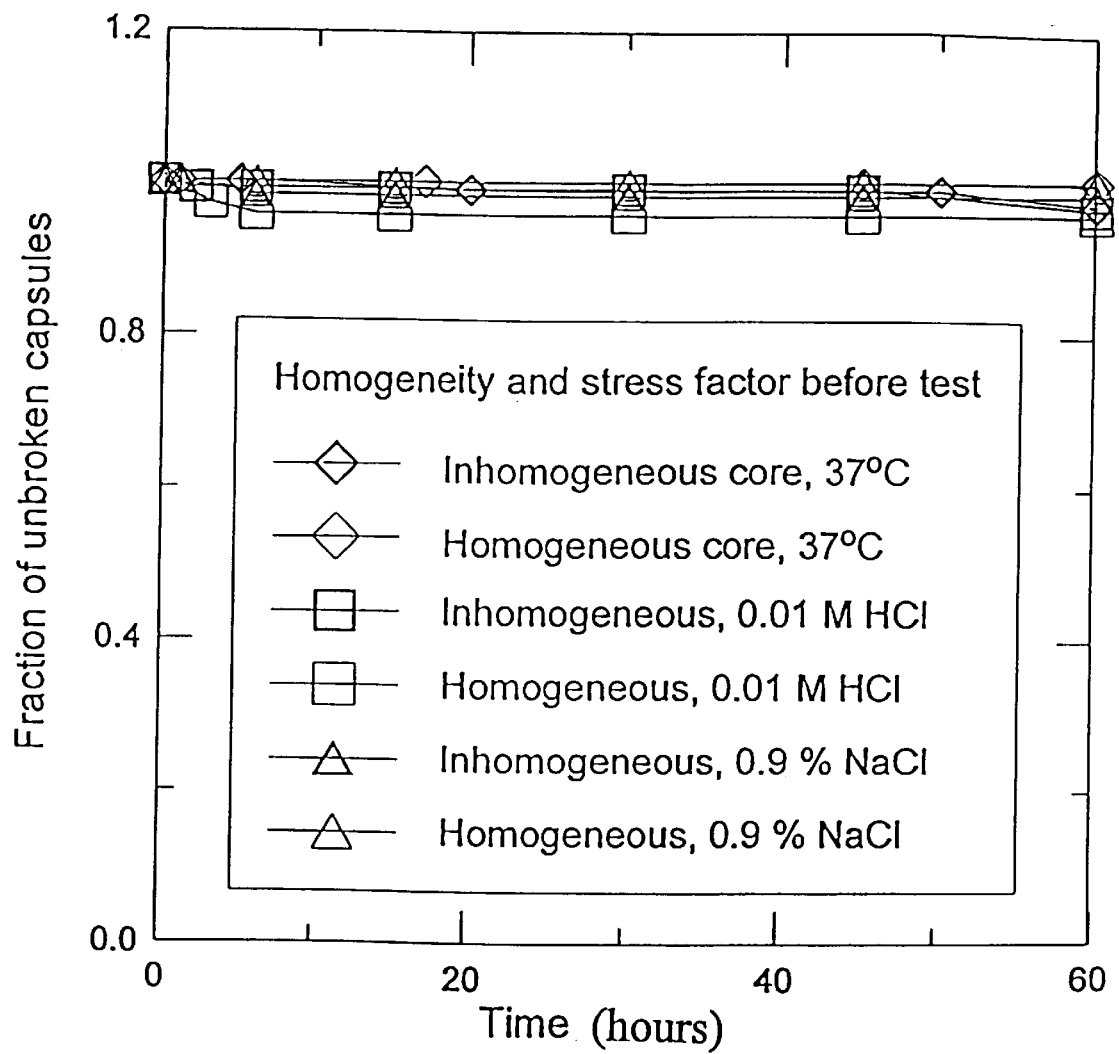
FIG. 15 illustrates the stability in various environments of capsules prepared according to the invention.

FIG. 15 shows the results of an explosion assay demonstrating the strength of capsules prepared according to the process of the invention and subjected to various environments mimicking those of the body. It is evident that the capsules of the invention show excellent stability in these environments over a long period of time of at least 60 hours.

Figure 16:
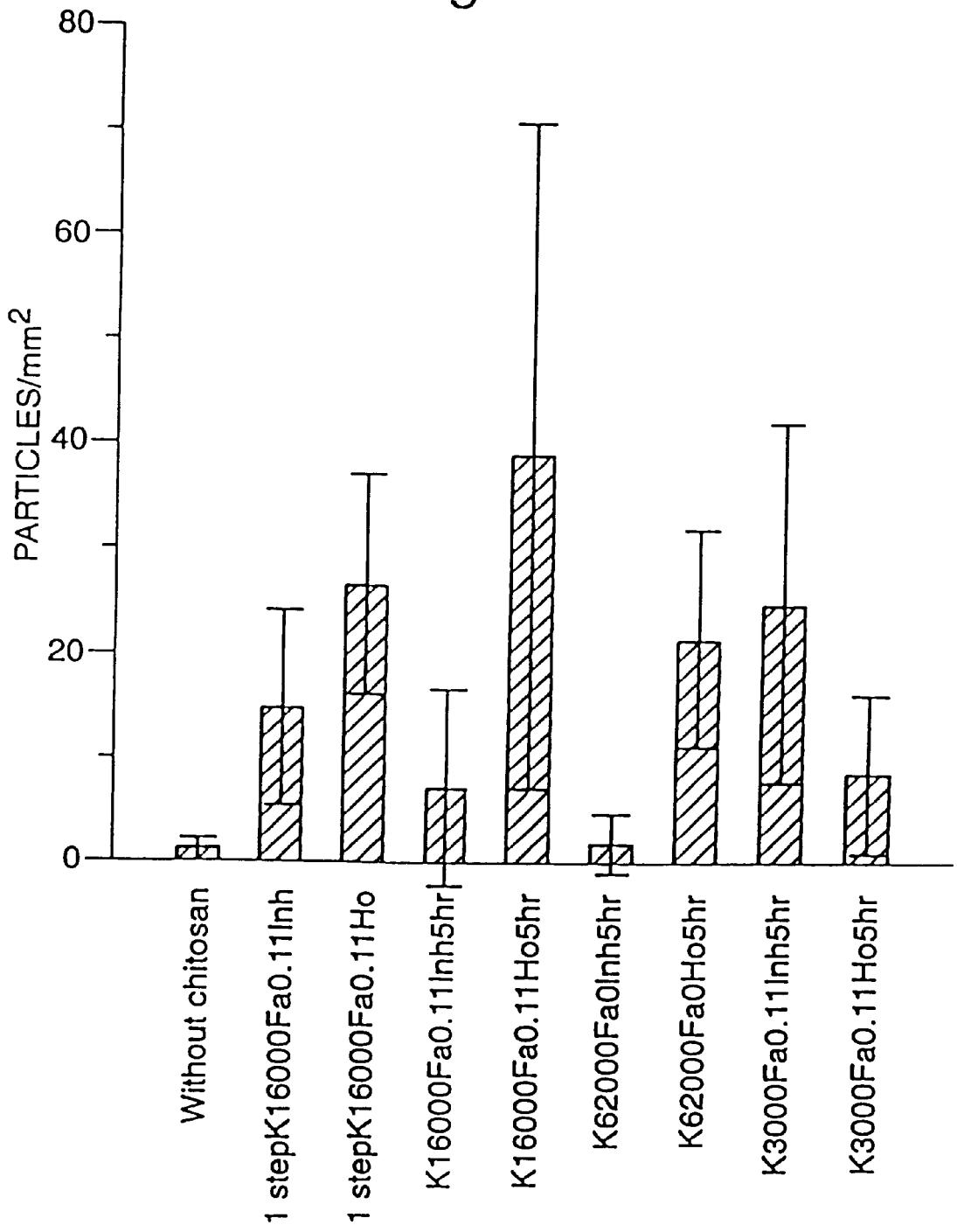
FIG. 16 illustrates the adhesion capacity for negatively charged particles of alginate-chitosan capsules having homogeneous and inhomogeneous cores and prepared according to the method of the present invention and a prior art method.

FIG. 16 shows a comparison of the adhesion capacity for negatively charged particles of capsules prepared according to the invention and capsules prepared according to the prior art one-step process. All capsules were prepared with both homogeneous and inhomogeneous alginate cores, and for the capsules prepared according to the process of the invention, two different chitosan molecular weights were tested.

In FIG. 16:

"1 step" refers to capsules made by the prior art one step process;

"K" represents the molecular weight, of the chitosan used, in Daltons. Thus, K16000 refers to a chitosan molecular weight of 16000 Da;

"Fa" represents the fraction of acetylation of the chitosan used;

"Ho" represents capsules with a homogenous alginate core;

"Inh" represents capsules with an inhomogenous alginate core;

"5hr" refers to the reaction time of the membrane forming step, which was five hours in each case.

EXAMPLES

The following examples are illustrative of the capsules of the invention and their uses.

Example 1

Capsules effective in the treatment of gastro-oesophageal reflux

Active Ingredient: Calcium Carbonate

Ingredients:

Sodium alginate

Chitosan Chloride (low molecular weight around 16000 Da to give highest level of coating)

Calcium chloride

Buffer ingredients (sodium acetate and acetic acid)

Water qs

Method:

1. Dissolve the sodium alginate in sufficient water to give a 2% solution and add the calcium carbonate to give a 12% w/v dispersion and stir until dispersed. Prepare a solution containing 50 mM calcium (as chloride) and 200 mM sodium chloride.

2. Form beads of sodium alginate containing calcium carbonate by adding the alginate calcium carbonate solution/suspension dropwise into the calcium chloride solution.

3. Coat the beads with chitosan by gently stirring the alginate beads in a solution of 0.15% chitosan chloride containing 300 mM of calcium (as chloride) to form the microcapsules. This solution is buffered to pH 5 using a sodium acetate buffer at a concentration of 0.02 M. The beads are then washed in the sodium acetate buffer.

4. Concentrate the capsules such that on shaking the bottle a 10 ml spoonful can be dispensed that will contain one 300 mg dose of calcium carbonate in 10 ml. Add preservatives, colour, sweetener and/or flavour as required prior to achieving final volume.

Use:

On ingesting one 10 ml spoonful the capsules adhere to the oesophageal mucosa to provide a slow releasing source of calcium carbonate to neutralise any acid refluxed from the stomach for treating heartburn.

Advantage:

This product adheres to the affected site providing local acid neutralisation and relief from heartburn caused by acid on the oesophageal mucosa.

Example 2

Capsules effective in the treatment of sore throat.

Active ingredient: Lignocaine base

Method:

Other ingredients and method of manufacture—as example (1) stages 1–3 but replacing the calcium carbonate with a fine powder of lignocaine base in a quantity sufficient to give a 0.6% w/v dispersion.

Add flavour, sweetener and preservatives as required and concentrate the capsules so that 1 ml contains capsules holding a dose of 3 mg of lignocaine base.

Use:

Approximately 1 ml of suspension of adherent capsules is sprayed on to the throat to provide a local anaesthetic effect for treating sore throats.

Advantage:

The capsules adhere to the throat and release the active ingredient slowly to provide a sustained pain killing effect.

Example 3

Taste masking of drugs for release in the stomach.

Active ingredient:

Cimetidine hydrochloride

Method:

Other ingredients and method of manufacture—as example (1) stages 1–3 but replacing the calcium carbonate with a fine powder of cimetidine hydrochloride in a quantity sufficient to achieve 4% w/v.

A high molecular weight chitosan 63000 Da with a short incubation time was used to give only a thin coating—this gives taste masking but minimises the delay to drug release which could otherwise occur due to slow diffusion through a thick coating of chitosan.

Concentrate the capsules so that on shaking the bottle a 10 ml spoonful can be dispensed that will contain one 200 mg dose of cimetidine in 10 ml. Add preservatives colour sweetener, flavour as required prior to achieving final volume.

Use and advantage:

The suspension is used to treat dyspepsia and heartburn. Cimetidine is a well known agent for such treatments but suffers from an unacceptable taste in traditional solution formulations. Incorporation of the drug into the capsule system enables the taste of the drug to be masked during its presence in the mouth.

Example 4

Capsules adherent to the stomach mucus/mucosa for release of drugs into the stomach.

Active ingredient: Triclosan

Method:

Other ingredients and methods of manufacture—as example (1) stages 1–3 but replacing the calcium carbonate with a fine powder of triclosan in a quantity sufficient to achieve a 3% w/v dispersion.

Concentrate the capsules such that on shaking the bottle a 10 ml spoonful can be dispensed that will contain one 150 mg dose of triclosan in 10 ml. Add preservatives colour sweetener, flavour as required prior to achieving final volume.

Use: The suspension is used to treat Helicobacter Pylori infections. The capsules adhere to the mucus lining the stomach to provide a slow release of the Triclosan which has antibacterial activity against *H. pylori*.

Advantage:

The drug is retained at the site of action for longer periods than a for a simple suspension giving a more effective action against this organism.

What is claimed is:

1. A process for preparing high strength capsules comprising:
   (a) preparing gelled beads of a polyanionic polysaccharide which are cross-linked with a polyvalent cation,
   (b) forming capsules having a polycation-polyanion membrane layer on the gelled beads by adding the beads to a solution comprising a polycationic polysaccharide,
   (c) optionally forming one or more polycationic or polyanionic layers on the capsules, and
   (d) harvesting the resulting capsules, wherein the process further comprises providing a polyvalent cation in the polycationic polysaccharide solution of (b).

2. The process as claimed in claim 1, wherein (a) comprises:
   (i) providing a first solution comprising the polyanionic polysaccharide,
   (ii) providing a second solution comprising the cross-linking polyvalent ions and a non-gelling ion, and
   (iii) adding the first solution in drops to the second solution, thereby to prepare homogeneous capsules.

3. The process as claimed in claim 1, further comprising providing a solution of a non-gelling ion, and immersing the beads of (a) in the solution of non-gelling ion, thereby preparing homogeneous capsules.

4. The process as claimed in claim 1, further comprising including an active ingredient, material or substance in the gelled bead of (a).

5. The process as claimed in claim 4, wherein the active ingredient, material or substance is encapsulated in the gelled bead.

6. The process as claimed in claim 4, wherein the active ingredient, material or substance is selected from one or more of pharmaceutically active materials, catalysts, living or dead cells, tissue, pesticides, herbicides, agricultural nutrients or fertilisers, seeds, cosmetic products or food ingredients.

7. The process as claimed in claim 1 wherein the polyanionic polysaccharide is an alginate.

8. The process as claimed in claim 7, wherein the alginate has a G-block content of at least 50%.

9. The process as claimed in any of claim 1, wherein the polyanionic polysaccharide is pectin.

10. The process as claimed in claim 1, wherein the polycationic polysaccharide includes imino or amino groups.

11. The process as claimed in claim 10, wherein the polycationic polysaccharide is chitosan.

12. The process as claimed in claim 11, wherein the chitosan has a molecular weight in the range of from 5,000 to 60,000.

13. The process as claimed in claim 11, wherein the chitosan has a molecular weight of from 60,000 to 100,000.

14. The process as claimed in claim 1, wherein the polyvalent cation of (e) is selected from calcium, strontium, barium, aluminium (III) or iron (III).

15. The process as claimed in any preceding claim wherein the polyvalent cation in the membrane forming step (step (e)) is present at a concentration of from 50 mM to 400 nm.

16. The process as claimed in claim 2, wherein the non-gelling ion is present at a concentration of at least 10 mM.

17. The process as claimed wherein (step (b) proceeds for at least 30 minutes.

18. The process as claimed in claim 2, wherein the (step (b) proceeds for at least 15 minutes.

19. Capsules obtainable by the process of claim 1.

20. The capsules as claimed in claim 19, wherein the diameter of the capsules is from 0.1 mm to 1.0 mm.

21. Capsules obtainable by the process of claim 6, wherein the active ingredient, material or substance is a pharmaceutically active ingredient.

22. The capsules as claimed in claim 21, wherein the pharmaceutically active ingredient is an acid neutralising agent.

23. The capsules as claimed in claim 21, wherein the pharmaceutically active ingredient is a local anaesthetic.

24. The capsules as claimed in claim 21, wherein the pharmaceutically active ingredient is a histamine $H_2$_receptor antagonist.

25. The capsules as claimed in claim 21, wherein the pharmaceutically active ingredient is an anti-microbial agent.

26. Capsules obtainable by the process of claim 4 wherein the active ingredient, material or substance is selected from one or more catalysts, living or dead cells, tissue, pesticides, herbicides, agricultural nutrients or fertilisers, seeds, cosmetic products or food ingredients.

27. The process of claim 2, wherein the non-gelling ion is a sodium ion.

28. The process of claim 3, wherein the non-gelling ion is a sodium ion.

29. The process of claim 8, wherein the alginate has a G-block content of 60 to 75%.

30. The process of claim 12, wherein the chitosan has a molecular weight in the range from 10,000 to 30,000.

31. The process of claim 14, wherein the polyvalent ion is calcium.

32. The process of claim 15, wherein the concentration of the non-gelling ion is from 100 mM to 300 mM.

33. The process of claim 16, wherein the concentration of the non-gelling ion is from 100 mM to 300 mM.

34. The process of claim 17, wherein (b) proceeds for 2 to 5 hours.

35. The process of claim 17, wherein (b) proceeds for 1 to 2 hours.

36. The process of claim 18, wherein (b) proceeds for 2 to 5 hours.

37. The process of claim 18, wherein (b) proceeds for 1 to 2 hours.

38. The capsules as claimed in claim 20, wherein the diameter is from 0.2 mm to 0.7 mm.

39. The capsules as claimed in claim 38, wherein the diameter is from 0.3 mm to 0.4 mm.

40. A method of treating gastro-oesphagael reflux comprising administering the capsules of claim 22 to a patient in need of such treatment.

41. A method of treating a sore throat comprising administering the capsules of claim 23 to a patient in need of such treatment.

42. A method of treating dyspepsia or heartburn comprising administering the capsules of claim 24 to a patient in need of such treatment.

43. A method of treating a *Heliobactor pylori* infections comprising administering the capsules of claim 25 to a patient in need of such treatment.

44. A pesticidal, herbicidal, agricultural, nutrient or fertilizer preparation comprising the capsules of claim 26.

45. A process for preparing high strength capsules consisting essentially of:
  (a) preparing gelled beads of a polyanionic polysaccharide which are cross-linked with a polyvalent cation,
  (b) forming capsules having a polycation-polyanion membrane layer on the gelled beads by adding the beads to a solution comprising a polycationic polysaccharide,
  (c) optionally forming one or more polycationic or polyanionic layers on the capsules, and
  (d) harvesting the resulting capsules, wherein a polyvalent cation is provided in the polycationic polysaccharide solution of (b).

* * * * *